(12) United States Patent
Marchitto et al.

(10) Patent No.: US 7,588,565 B2
(45) Date of Patent: Sep. 15, 2009

(54) METHOD AND DEVICE FOR ANASTOMOSES

(75) Inventors: Kevin S. Marchitto, Golden, CO (US); Stephen T. Flock, Arvada, CO (US)

(73) Assignee: Rocky Mountain Biosystems, Inc., Golden, CO (US)

( * ) Notice: Subject to any disclaimer, the term of this patent is extended or adjusted under 35 U.S.C. 154(b) by 515 days.

(21) Appl. No.: 10/438,514

(22) Filed: May 15, 2003

(65) Prior Publication Data
US 2003/0236518 A1 Dec. 25, 2003

Related U.S. Application Data

(60) Provisional application No. 60/380,817, filed on May 15, 2002.

(51) Int. Cl.
*A61B 18/18* (2006.01)
*A61B 17/08* (2006.01)
(52) U.S. Cl. .................. 606/27; 606/214; 600/13
(58) Field of Classification Search ............ 606/27–31, 606/41, 213–216; 600/13; 607/98–101
See application file for complete search history.

(56) References Cited

U.S. PATENT DOCUMENTS

| | | | | |
|---|---|---|---|---|
| 3,653,385 A * | 4/1972 | Burton | .......... | 606/27 |
| 4,889,120 A * | 12/1989 | Gordon | .......... | 606/216 |
| 5,178,618 A * | 1/1993 | Kandarpa | .......... | 606/28 |
| 5,571,153 A | 11/1996 | Wallsten | .......... | 607/606 |
| 5,634,936 A * | 6/1997 | Linden et al. | .......... | 606/213 |
| 5,749,895 A * | 5/1998 | Sawyer et al. | .......... | 606/214 |
| 5,797,903 A | 8/1998 | Swanson | .......... | 606/606 |
| 6,238,421 B1 * | 5/2001 | Gunther et al. | .......... | 607/13 |
| 6,458,127 B1 * | 10/2002 | Truckai et al. | .......... | 606/49 |
| 6,786,904 B2 * | 9/2004 | Doscher et al. | .......... | 606/28 |

* cited by examiner

*Primary Examiner*—Michael Peffley
(74) *Attorney, Agent, or Firm*—Benjamin Aaron Adler

(57) ABSTRACT

Provided herein is a device for use in an anastomosis of tissue(s) comprising a biocompatible material and a means of applying radiofrequency energy or electrical energy to generate heat within said biocompatible material. The device also may be used to bond or fuse at two materials where at least one of the material is a tissue. Also provided are methods to anastomose tissue or to bond or to fuse these materials using these devices.

32 Claims, 14 Drawing Sheets

125a  125b 135a  135b

METHOD AND DEVICE FOR ANASTOMOSES

CROSS-REFERENCE TO RELATED APPLICATIONS

This non-provisional applications claims benefit of provisional U.S. Ser. No. 60/380,817, filed May 15, 2002, now abandoned.

BACKGROUND OF THE INVENTION

1. Field of the Invention

The present invention relates generally to the fields of biomedical engineering and surgery. More specifically, the present invention provides a device and methods for improving the ease with which anatomic structures can be anastamosed.

2. Description of the Related Art

There has been an effort recently to identify biocompatible molecules which can be used as a "tissue solder". Biomolecules such as fibrin, elastin, albumin have been or are used to "glue" tissue-to-tissue. A number of patents describe the "activation" of these biomolecules to form "welds" through irradiation, often in the form of laser radiant energy, but sometimes in the form of ultrasound or radiofrequency waves. The applied energy is believed to denature the molecules, which then adhere to one-another, or cross-link thereby effecting a union between the tissues.

Over the past fifteen years, a significant amount of scientific research has focused on using laser heated "solder" for "welding" tissues such as blood vessels (1-2). Research has been done on laser tissue welding with albumin solders which are an improvement over conventional suture closure because it offers an immediate watertight tissue closure, decreased operative time, especially in microsurgical or laparoscopic applications, reduced trauma, and elimination of foreign body reaction to sutures, collagen-based plugs and clips. The procedure has been enhanced with the use of advanced solders, strengthening structures, concurrent cooling, and added growth factors as disclosed, for example, in U.S. Pat. No. 6,221,068.

Use of lasers for tissue welding appeared very promising, however, the techniques have certain limitations. The laser energy must be manually directed by the surgeon which leads to operator variability. Additionally, the radiant energy is not dispersed evenly throughout the tissue. The high energy at the focal point may result in local burns and the heating effect drops off rapidly at a small distance from the focal point. Finally, lasers are expensive and currently cannot be miniaturized easily.

U.S. Pat. No. 5,669,934 describes a method for joining or restructuring tissue by providing a preformed film or sheet of a collagen and/or gelatin material which fuses to tissue upon the application of continuous inert gas beam radiofrequency energy. Similarly, U.S. Pat. No. 5,569,239 describes laying down a layer of energy reactive adhesive material along the incision and closing the incision by applying energy, either optical or radiofrequency energy, to the adhesive and surrounding tissue. Further U.S. Pat. No. 5,209,776 and U.S. Pat. No. 5,292,362 describe a tissue adhesive that is intended for use principally in conjunction with laser radiant energy to weld severed tissues and/or prosthetic material together.

U.S. Pat. No. 6,110,212 describes the use of elastin and elastin-based materials which are biocompatible and can be used to effect anastomoses and tissue structure sealing upon the application of laser radiant energy. Both U.S. Patent Application No. 20020045732 and U.S. Pat. No. 6,221,335 teach joining living tissues by using laser radiant energy to heat a "solder" consisting of protein, water and a compound which absorbs the laser radiant energy, preferably indocyanine green. This solder is optionally in the form of a tubular structure which can more easily be applied when vascular anastomoses are required. The stated benefits, inter alia, are the biocompatible and ubiquitous nature of elastin.

U.S. Pat. No. 6,302,898 describes a device to deliver a sealant and energy to effect tissue closure. It also discloses pre-treating the tissue with energy in order to make the subsequently applied sealant adhere better. PCT Publication WO 99/65536 describes tissue repair by pre-treating the substantially solid biomolecular solder prior to use. U.S. Pat. No. 5,713,891 discloses the addition of bioactive compounds to the tissue solder in order to enhance the weld strength or to reduce post-procedure hemorrhage.

U.S. Pat. No. 6,221,068 discloses the importance of minimizing thermal damage to the tissue to be welded. The method employs pulsed laser irradiation followed by cooling the tissue to nearly the initial temperature between each heating cycle. U.S. Pat. No. 6,323,037 describes the addition of an "energy converter" to the solder mixture such that optical energy will be efficiently and preferentially absorbed by the solder which subsequently effects a tissue weld.

Common problems exist throughout the prior art. These include tissue damage due to uneven heating, unknown and/or uncontrollable thermal history, i.e., time-temperature profile, and relatively high cost. It is notable that a consistent means of treatment and control are desirable. The Code of Federal Regulations, 21 CFR 860.7(e)(1), establishes that there is "reasonable assurance that a device is effective when it can be determined, based upon valid scientific evidence, that in a significant portion of the target population, the use of the device will provide clinically significant results." Devices that cannot be shown to provide consistent results between patients, or even within a patient upon multiple use, will have minimal utility and may not be approved, if approved, for broad use. Beyond devices, it is generally desirable to develop medical products with critical controls that can deliver precise results.

Inductive heating (3) is a non-contact process whereby electrical currents are induced in electrically conductive materials (susceptors) by a time-varying magnetic field. Generally, induction heating is an industrial process often used to weld, harden or braze metal-containing parts in manufacturing where control over the heating process and minimized contact with the workpiece are critical.

Basically, radiofrequency power is coupled to a conducting element, such as a coil of wire, which serves to set up a magnetic field of a particular magnitude and spatial extent. The induced currents or Eddy currents flow in the conductive materials in a layer referred to as the skin depth $\delta$ (m), given by:

$$\delta = \sqrt{/(2\rho/\mu\Omega)},$$

where $\Omega$ is frequency (rads/s), $\rho$ is resistivity (ohm-m) and $\mu$ is the permeability (Webers/amp/m) which is the product of $\mu o$ the permeability of free space and $\mu r$ the relative permeability of the material.

The magnetic permeability of a material is quantification of the degree to which it can concentrate magnetic field lines. Note, however, that the permeability is not constant in ferromagnetic substances like iron, but depends on the magnetic flux and temperature. The skin depth at room temperature at 1 MHz electromagnetic radiation in copper is 0.066 mm and in 99.9% iron is 0.016 mm.

The consequence of current flowing is Joule, or $I^2R$, heating. The skin-depth formula leads to the conclusion that, with increased frequency, the skin depth becomes smaller. Thus, higher frequencies favor efficient and uniform heating of smaller components. In certain situations localized heat can also be generated through hysteresis losses or frictional heating, referred to as dielectric hysteresis heating in non-conductors, as the susceptor moves against physical resistance in the surrounding material. Consideration of Joule heating alone results in a formula for the power-density P (W/cm$^3$) in the inductively-heated material:

$P=4\pi H^2 \mu_0 \mu_r f M$, where H is the root-mean-square magnetic field intensity (A/m), f is frequency (Hz), M is a power density transmission factor (unitless) which depends on the physical shape of the heated material and skin depth and diameter of the part to be heated (4-5).

M, which is equal to the product of F and d/d where F is a transmission factor and d is the diameter of the part, can be shown to be maximally about 0.2 when the object diameter is 3.5 times the skin depth and when certain other assumptions are made. Thus, for a given frequency there is a diameter for which the power density is a maximum; or equivalent, there is a maximum frequency for heating a part of a certain diameter below which heating efficiency drops dramatically and above which little or no improvement of heating efficiency occurs. It can also be shown that the power density of inductively heated spheres is much higher than solid spheres of the same material.

There are only a few examples of the use of inductive heating in the medical literature. The oldest example of use of therapeutic inductive heating is in hyperthermia of cancer, whereby large metallic "seeds" are inductively heated using a coil external to the body (6). Smaller seeds were used where small biocompatible dextran magnetite particles in magnetic fluid was used to treat mouse mammary carcinoma by hyperthermia (7). U.S. Patent Application Ser. No. 2002/0183829 describes inductively heating stents made of alloys with a high magnetic permeability and low curie temperature for the purpose of destroying smooth muscle cells in restenosing blood vessels. A more recent report described the diagnostic use of induction heating to heat nanocrystals coupled to DNA in order to locally denature DNA for the purpose of hydridization (8.) The literature is deficient in descriptions whereby biomolecules are heated through induction. U.S. Pat. No. 6,348,679 discloses compositions used in bonding two or more conventional materials where the interposed composition consists of a carrier and a susceptor, which may be at least in part composed of certain proteins. However the applications apply to conventional substrates such as films or wood.

The inventors have recognized an increased need in the art for a precision device and improved methods of joining tubular, planar or irregular-surfaced tissues to other tissue structures or to dressings. Further, the prior art is deficient in devices and methods for minimally-invasive methods that use electromagnetic energy to controllably alter a biocompatible structure thereby making it adhere to tissue through molecular alterations and/or mechanical shrinkage. The present invention fulfills this longstanding need and desire in the art.

SUMMARY OF THE INVENTION

The present invention is directed to a device for use in an anastomosis of tissue(s) comprising a biocompatible material and a means of applying radiofrequency energy or electrical energy to generate heat within the biocompatible material.

The present invention also is directed to a device for bonding at least two materials, whereby at least one material is a tissue. The device comprises a biocompatible material, a means of applying radiofrequency energy or electrical energy to generate heat within the biocompatible material and a means of controlling output of the heat generated within the biocompatible material conducted to the materials to be bonded or fused.

The present invention is directed further to methods of anastomosis of at least one tissue or to methods of bonding or fusing at least two materials at least one of which is a tissue using the devices described herein.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
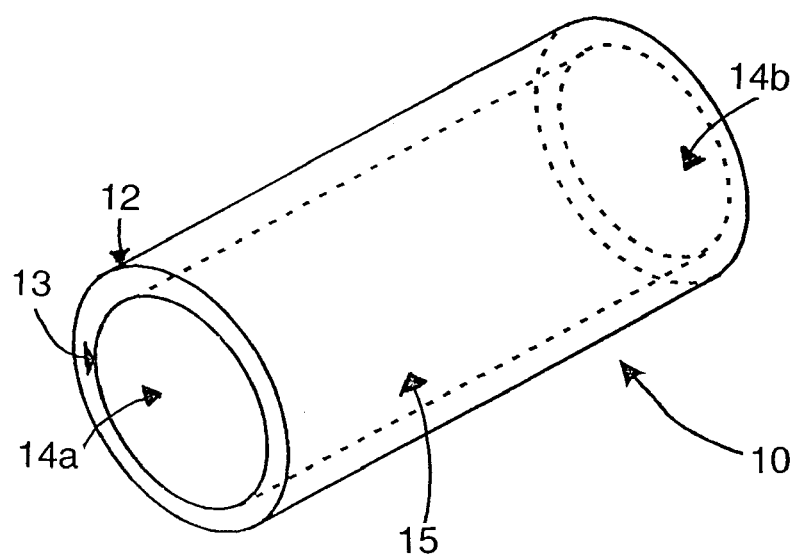
FIG. 1 depicts one embodiment of the device, essentially tubular in shape, used for vascular or tubular structure anastomoses.

In one embodiment of the present invention there is provided a device for use in an anastomosis of tissue(s) comprising a biocompatible material and a means of applying radiofrequency energy or electrical energy to generate heat within the biocompatible material. In all aspects of this embodiment the biocompatible material may conform to the tissue geometry. The biocompatible material may be a liquid, a solid or a semi-solid. Further, in all aspects the device may be used endoscopically.

In this embodiment the biocompatible material may comprise a protein, a biocompatible polymer, polymeric matrix substance, or a combination thereof. Examples of a protein is elastin, albumin, fibrin, collagen, or glycoprotein. Representative examples of a polymeric substance is hydrogel, agar or sol-gel. Furthermore the biocompatible material may comprise a pharmaceutical. The pharmaceutical may be an anticoagulant, an antithrombotic, an antibiotic, a hormone, a steroidal antiinflammatory agent, a non-steroidal antiinflammatory agent, an anti-viral agent or an anti-fungal agent.

In one aspect of this embodiment the means to apply electrical energy to the biocompatible material comprises at least one electrode in electrical contact with the biocompatible material. In a related aspect the means to apply radiofrequency energy to the biocompatible material comprises at least one induction coil proximate to the device where the induction coil(s) generates an oscillating magnetic field around the device. The induction coil(s) may further comprise a cooling means having a cooling fluid and a containment means for the cooling fluid. Examples of a cooling fluid are low viscosity mineral oil or water. The containment means may be a glass envelope containing the cooling fluid and the induction coil(s) or may be copper tubing containing the cooling fluid. Further to this aspect the induction coils may comprise a coating of a smooth non-adhering material. Examples of a non-adhering material are teflon, titanium or gold.

In a related aspect the device may further comprise a clamp-like instrument having two arms pivotally connected at the center for scissors-like action. The first ends of the arms are attached to the induction coils. The second ends of the arms function as a handle with which to manipulate and position the induction coils proximate to the device.

In another aspect of this embodiment the device comprises a means of controlling output of the heat generated within the biocompatible material conducted to the tissues. The heat control means comprises a conductive material in contact with the biocompatible material. The conductive material has a thermal history such that application of radiofrequency energy or electrical energy to the conductive material generates an estimable amount of heat. The conductive material may be a metal wire, a metal particle, a ferromagnetic material, a paramagnetic material, a conducting polymer, an ionic molecule, a polar molecule or a conducting microsphere. Additionally, the conductive material may be an energy-absorbing material, said energy-absorbing material comprising conducting polystyrene microbeads, a colloidal metal, a conducting polymer, a strongly ionic molecule or a strongly polar molecule.

In another embodiment of the present invention there is provided a method for performing an anastomosis between at least two tissues comprising the steps of positioning the device described supra around the tissues such that the tissues simultaneously contact the biocompatible material of the device and each other, applying radiofrequency energy or electrical energy to the biocompatible material and generating heat within the biocompatible material and the tissues whereby the heating adheres the biocompatible material to the tissues or adheres the tissues to each other thereby anastomosing the tissues. In this embodiment adherence of the biocompatible material to the tissues or of adherence of the tissues results from molecular changes in the biocompatible material and said tissues. The features of the device, e.g., biocompatible materials, energy sources, induction coils, cooling means, heat output control means, conductive elements, or pharmaceuticals, are as described supra.

In yet another embodiment of the present invention there is provided a device for bonding or fusing at least two materials, whereby at least one material is tissue, comprising a biocompatible material, a means of applying radiofrequency energy or electrical energy to generate heat within the biocompatible material and a means of controlling output of the heat generated within the biocompatible material conducted to the materials to be bonded or to be fused. In all aspects of this embodiment the features of the device, e.g., biocompatible materials, energy sources, induction coils, cooling means, heat output control means, conductive elements, or pharmaceuticals, are as described supra.

In still another embodiment of the present invention there is provided a method for bonding or fusing two materials, whereby at least one is tissue, comprising the steps of positioning the device described supra around the materials whereby the materials simultaneously contact the biocompatible material of the device and each other, applying radiofrequency energy or electrical energy to the biocompatible material, generating heat within the biocompatible material; and controlling output of the heat to the materials to be bonded or to be fused via the heat controlling means of the device such that the output of heat bonds the biocompatible material to the materials to be bonded or fuses the materials together. In this embodiment bonding of the biocompatible material to the materials or fusing the materials together results from molecular changes in the biocompatible material and in the materials. Again the features of the device, e.g., biocompatible materials, energy sources, induction coils, cooling means, heat output control means, conductive elements, or pharmaceuticals, are as described supra.

Provided herein are methods for inductively heating non-conventional substrates, i.e. biological materials, in order to cause conformational changes that result in unique properties with regard to tissues. In particular, methods, devices and compositions are disclosed whereby the principles of induction heating are applied to heat biological materials and cause them to join to one another or to non-biological materials. Particularly, upon inductive heating, proteins, and possibly other biomolecules, present in the tissues take part in a fusion process that allows tissues to adhere to one another. The fusion process may involve the addition of adhesives between the tissues that could include susceptors that assist the process of inductive coupling.

Generally, the present invention relates to a device and method for heating a liquid, solid or semi-solid composition to be utilized in the human body for bonding tissues or filling defects in tissues. The device comprises a source of radiofrequency (RF) energy coupled to an applicator, which then produces an oscillating magnetic field, and the composition which inductively couples with the magnetic field resulting in the transient production of heat substantially within the composition. The consequences of heat are molecular changes in the composition resulting in fusion with the adjacent tissue. The adjacent tissue also may take part in the fusion process by being altered by the transient presence of heat.

In the present invention inductive coupling most simply results in heating, via magnetization, particles or other ionic species, either having non-zero conductivity and magnetic permeability, impregnated in a biocompatible fusion composition or adhesive. The composition may be comprised largely of a protein, e.g., serum albumin, with the addition of a metal such as 300 mesh nickel flakes. The induced electrical currents produced in the particles results in heat which then conducts into the area immediately surrounding the metal, resulting in a "melting" of the adhesive and perhaps the adjacent tissue. Less than a second later, when the adhesive cools, it forms a bond with the tissue.

The adhesion effect may be a consequence of the proteins in the fusion formulation bonding, perhaps by crosslinking, with other molecules in the protein formulation as they cool, as well as the proteins in the adhered tissue. This may be considered as a "bridge" between the molecules and a "scaffold" between the tissues. The endogenous proteins in the tissue also may have been denatured and coagulated due to nearby heat production which may be critical to the adhesion strength.

It is contemplated that in tissue the temperatures needed to achieve a bond range from about 45-85° C. and that the heating times are very short since protein denaturation is essentially instantaneous once a critical temperature is achieved. Thus, the powers required for the present device and method are far less than those used in commercially available industrial induction-heating devices which are used for welding metals and plastics. Accordingly, the present invention can be produced for a fraction of the cost of commercial devices.

The source of RF energy provides electrical energy to a probe which comprises an electrically conducting material, such as copper, wound in the shape of a solenoid or coil. Other probe shapes may prove more suitable for particular applications. The conducting material may be hollow or may be solid. The probe may be cooled. If the conducting material comprising the probe is hollow, a cooling fluid can be circulated within its lumen. The solid probe material may be positioned within a liquid-tight envelope such that coolant, preferably one of low electrical permitivity, e.g. mineral oil, can be circulated around it to keep it from overheating.

The conducting material comprising the probe sets up an oscillating magnetic field which inductively couples to a conductive material in the biocompatible composition when the material is positioned within the magnetic field. Through physical movement of the conducting material and/or the establishing of eddy currents within the conducting material or the tissue and/or composition and/or hysteresis losses, heat is produced. The heat diffuses into the surrounding composition and tissue thereby causing protein denaturation and alteration of surrounding biomolecules, e.g. lipid melting. This heating results in conformational changes in the molecules which effect adherence in the tissues. In a simple case, depending on the protein, denaturation may result in links with adjacent molecules thus effecting the bond.

Thus, the present invention provides a tissue-fusion-device (TFD). The TFD operates by electromagnetically heating the biocompatible fusion compositions to create tissue bonds. The TFD comprises a fusion composition, an applicator and an activator.

Fusion Composition

The materials that comprise the fusion composition must be biocompatible, able to be inductively heated and able to produce a fusion in biomaterials. The fusion composition may comprise a biocompatible polymer, a protein such as albumin, elastin and/or collagen or polysaccharides, e.g. cellulose, starch, chitosan, alginate, emulsan, or pectin. Examples of biodegradable polymers are polylactide (PLA), polyglycolide (PGA), lactide-glycolide copolymers (PLG), polycaprolactone, lactide-caprolactone copolymers, polyhydroxybutyrate, polyalkylcyanoacrylates, polyanhydrides, and polyorthoesters. Examples of biocompatible polymers are acrylate polymers and copolymers such as methyl methacrylate, methacrylic acid, hydroxyalkyl acrylates and methacrylates, ethylene glycol dimethacrylate, acrylamide, bisacrylamide or cellulose-based polymers, ethylene glycol polymers and copolymers, oxyethylene and oxypropylene polymers, poly(vinyl alcohol), polyvinylacetate, polyvinylpyrrolidone and polyvinylpyridine. Optionally, protein primers, which are substances that exhibit groups that can crosslink upon the application of heat, can be added.

Proteins are particularly attractive in tissue bonding applications in that they typically denature at temperatures less than 100° C. Denaturation can lead to cross-linking with other molecules, particularly proteins, in the immediate environment while the proteins are still in the denatured state, or upon their renaturation. Additional materials added to the composition formulations may result in greater flexibility and tensile strength as well as optimum treatment times and temperatures. The formulations utilize commonly occurring tissue and proteins, such as albumin, collagen, elastin, but may also contain silk, lignin, dextran, or may contain soy-derivatives, poly-glutamic acid, combined with additives such as polyethylene glycol or hydrogel to improve the rheologic nature of the adhesive.

Optionally, hyaluronic acid can be added to the composition to enhance the mechanical strength of adhesives, such as is sometimes done in laser tissue welding, or pre-denaturation may take place before application of the composition at the treatment site. Other materials, such as fibrinogen or chitin or chitosan, may be added to the composition to provide hemostasis and/or some degree of immediate adhesion. Materials such as calcium phosphate or polymethylmethacrylate, also can be used, most beneficially when boney material is the tissue to be treated.

Additionally, pharmaceuticals, e.g., an anti-coagulant, an antithrombotic, an antibiotic, a hormone, a steroidal antiinflammatory agent, a non-steroidal anti-inflammatory agent, an anti-viral agent or an anti-fungal agent, may be beneficially added to the composition in order to provide some desirable pharmacologic event.

Optionally, destabilizing/stabilizing agents, e.g. alcohol, can be added as they have been shown to alter the denaturation temperature. For example, an increase in the concentration of NaCl, referred to as "salting-in" proteins, can increase the denaturation temperature of globulin, while an increase in the concentration of $NaClO_4$, or "salting-out", reduces the denaturation temperature (9). When proteins are exposed to either liquid-air or liquid-liquid interfaces, denaturation can occur because the protein comes into contact with a hydrophobic environment. If allowed to remain at this interface for a period of time, proteins tend to unfold and to position hydrophobic groups in the hydrophobic layer while maintaining as much charge as possible in the aqueous layer. Thus, by ultrasonically adding bubbles, e.g., of gas, to the composition will serve to lower the denaturation point of the mixture.

The conductive materials that can be inductively heated are added to the composition in amounts typically no more than 10% by weight, although other concentrations can be used, but not limited to 0.1-25%. The material may include salts or other ionic species, or metals of variable size. For example, nanometer sized particles to macroscopic sized particles up to 1 mm in size can serve as effective susceptors. Alternatively, the conductive material may take of the form of a fine conductive lattice or mesh, such as available from Alfa Aesar Inc (Ward Hill, Mass.).

Examples of conductive materials that may be useful by themselves or in alloys are, although not limited to, tantalum, niobium, zirconium, titanium, and platinum which are some of the most biocompatible elements. Additional conductive materials may be phynox, which is an alloy of cobalt, chromium, iron, nickel, molybdenum, palladium/cobalt alloy, magnetite, nitinol, nitinol-titanium alloy, titanium, which optionally may be alloyed with aluminum and vanadium at 6% Al and 4% V, tantalum, zirconium, aluminum oxide, nitonol which is a shape memory alloy, cobalt, which optionally may be alloyed with chromium, molybdenum and nickel, or, optionally, 96% Co/28% Cr/6% Mo alloy, iron, nickel, gold, palladium, and stainless steel, e.g., biocompatible type 316L. The conductive materials may take the shape of a mesh, fibers, macroscopic and solid materials, flakes or powder. The conductive materials may be anodized and may further be encapsulated in materials such as liposomes, compounds such as calcium phosphate, polystyrene microspheres, pharmaceuticals, hydrogels, or teflon. These encapsulating materials may minimize the chance of an immune response to the conductor, may induct a desirable pharmacologic event, or may enhance the inductive coupling to the activating magnetic field.

The rheology of the fusion composition can be important. For example, producing the composition in a low-viscosity liquid form would allow injection through a cylindrical pathway such as a trochar or working-channel of an endoscope. A higher viscosity material can be applied to a tissue and will stay in place prior to activation. A solid formulation could be shaped, for example, as a tube, which could be them be positioned in a tubular anatomical structure, e.g. blood vessel or ureter, thus providing mechanical support prior to activation.

Other shapes may be more appropriate for different procedures. For example, a flat-sheet of composition would be suitable for sealing a large area of skin or soft-tissue, while a solid cylinder could be most appropriate for placement in the cavity left behind after a cannula is extracted. A porous structure of the fusion formulation might be beneficial for the subsequent in-growth of cells. It is conceivable that the conductive material itself, when distributed throughout the treatment area, would employ the endogenous proteins in production adhesion thus precluding the use of an external protein in the formulation.

Cross-linked polymers are quite insoluble, but they can be swollen to different degrees depending on their cross-linking. Swelling can be initiated by changes in temperature, pH, solvent type, ionic strength, light intensity, pressure, and electromagnetic fields. Hydrogels can be made biologically inert or biodegradable and are easily derivatized, particularly with enzymes. They can be grafted or bonded onto other materials, even living tissue.

The equilibrium swelling degree or sorption capacity, i.e., swollen volume/dry volume, is one defining property of a hydrogel. Depending upon the formulation, the swelling degree can be widely varied as can the sorption rate, which is roughly proportional to the equilibrium swelling degree. Permeability to water, drugs, proteins, and other biomolecules can be varied over wide ranges depending upon the swelling degree or water content. Hydrogels may be a useful optional addition to the fusion formulation as they give it different thermal and mechanical properties and also allow for the incorporation of a pharmaceutical which can ultimately diffuse out of the fusion composition.

The biocompatible fusion composition may optionally have different additives depending on the material to which adhesion is required. For example, the material used in a vascular graft is typically manufactured from polytetrafluoroethylene (PTFE). The fusion composition could be prepared to preferentially adhere to PTFE. In one example, gelatinized PTFE, when used as one of the components of the fusion composition, could adhere to the PTFE in situ, thus effecting the desired result. This aspect is particularly important as it can result in the bonding of implantable materials, so they are stabilized, sealed or have materials bonded to them.

Furthermore, the fusion composition may incorporate a support lattice, such as can be made from poly(DL-lactide-co-glycolactide), silk or an inert material, such as teflon or nylon, or a conductive material such as fine stainless steel mesh. The support material would allow for the fusion composition to be formed into a particular geometric shape suitable for application to a particular anatomical structure.

For use in vascular anastomoses a preferable shape for the biocompatiblefusion material is tubular as shown in FIG. 1. The tube has an outer surface and an inner surface and a first open end and a second open end. The open ends are in parallel and have a diameter equal to a diameter across the inner surface of the tube.

Figure 2:
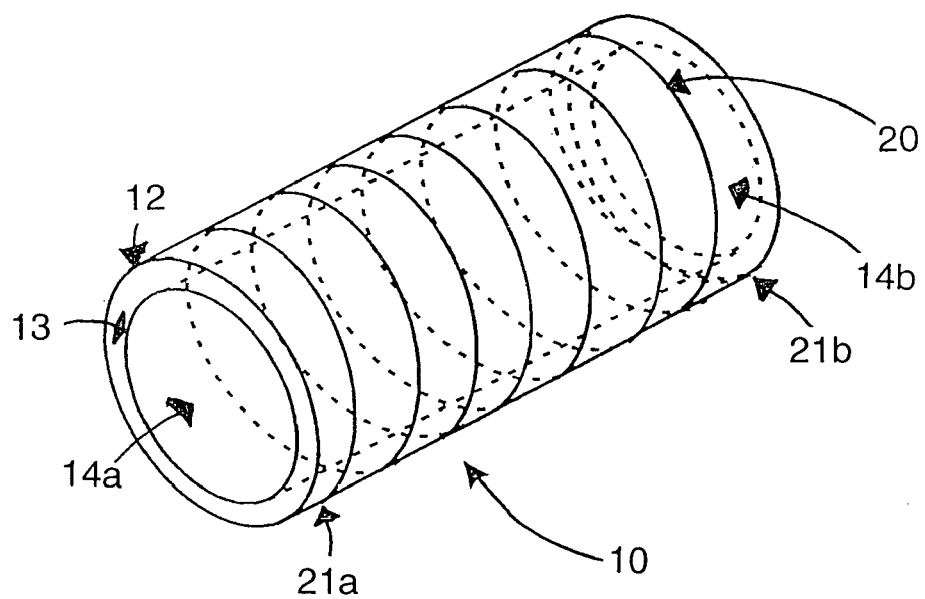
FIG. 2 depicts a conductive element positioned within the tubular device of FIG. 1.
Figure 3A:
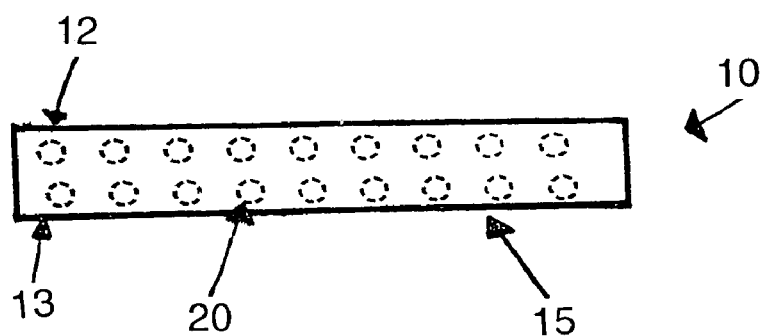
FIGS. 3A and 3B depict different placement geometries of the conductive heating elements within the material of tubular device of FIG. 2.
Figure 3B:
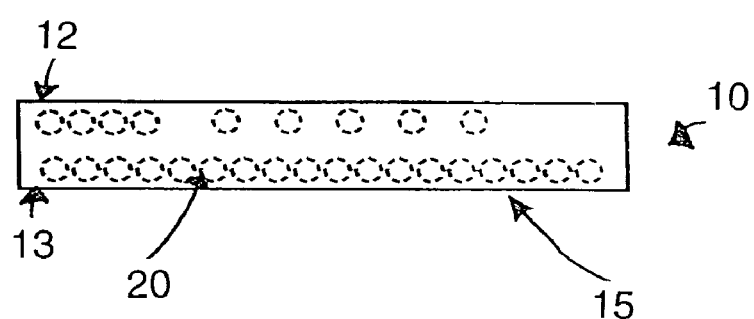

The tubular fusion composition may further comprise a conductive material or conductive element, such as a metal wire, that is helically shaped and uniformly coiled within the biocompatible material (FIGS. 2, 3A). Alternatively, the conductive element may be distributed asymmetrically within the biocompatible fusion material so that the element is positioned where heat distribution is preferable (FIG. 3B). The conductive element may optionally be positioned on the inside surface, the outside surface or on both surfaces of the tubular device for heat transfer to the tissue that is in contact with the biocompatible material in order to effect a bond. Application of electrical energy to each end of the helical conductive element by, for example, an electrode or induction of an alternating magnetic field around the device heats the conductive element to a critical temperature whereby the physical changes in the biocompatible material take place.

Figure 4:
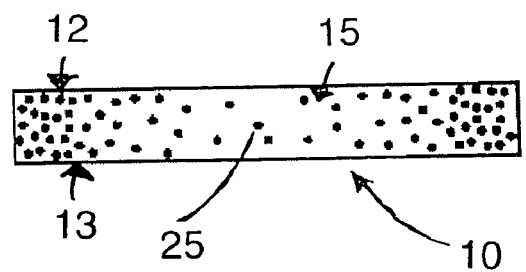
FIG. 4 depicts an inhomogeneous mixture of electric or magnetic field absorbing elements mixed within the material which makes up the tubular device.

The tubular fusion composition of the present invention may also contain an energy-absorbing material in addition to the biocompatible material that efficiently, as compared to human tissue, absorbs electromagnetic energy. Such energy-absorbing material is analogous to the conductive elements but are more particulate, i.e., not as macroscopic in structure as the conductive elements may be. The distribution of the energy-absorbing material may be such that more incident electromagnetic energy is absorbed where it is desired to produce more heat. This distribution is similar to the asymmetrical distribution of the conducting elements (FIG. 4). The energy-absorbing material may be, for example, conducting polystyrene microbeads, magnetic or metal-containing microbeads or nano-particles, colloidal metals, conducting polymers, or strongly ionic or polar molecules.

The tubular fusion material of the present invention is used to join tubular or approximately cylindrical anatomic structures, such as vascular vessels, to other tubular structures or to non-tubular structures. For example, in the situation where a patient is to undergo minimally invasive coronary artery bypass graft surgery (CABG), a surgeon gains endoscopic access to the obstructed cardiac blood vessel, whereupon dissection of the vessel at each end of the obstruction occurs. An appropriate length of a suitable bypass graft material, either man-made or a transplant, is positioned between the dissections. The first end of the tubular fusion material is fitted over the end of the healthy vessel in situ and the second end of the tubular fusion material is fitted over the bypass graft. The ends of the vessel and of the graft material are positioned to contact each other and a bond is effected between the vessel and the graft by applying RF to generate an external oscillating magnetic field or by applying a brief pulse of electrical energy to each end of the conductive element in the cylindrical device.

Alternatively, the ends of the healthy vessel and of the graft tissue are averted around the outer edge of the tubular fusion material. In this instance the tubular device may have an appended second part comprising the biocompatible fusion material. The appendage may also comprise the conducting element or the energy absorbing material embedded within the tubular material.

Figure 6A:
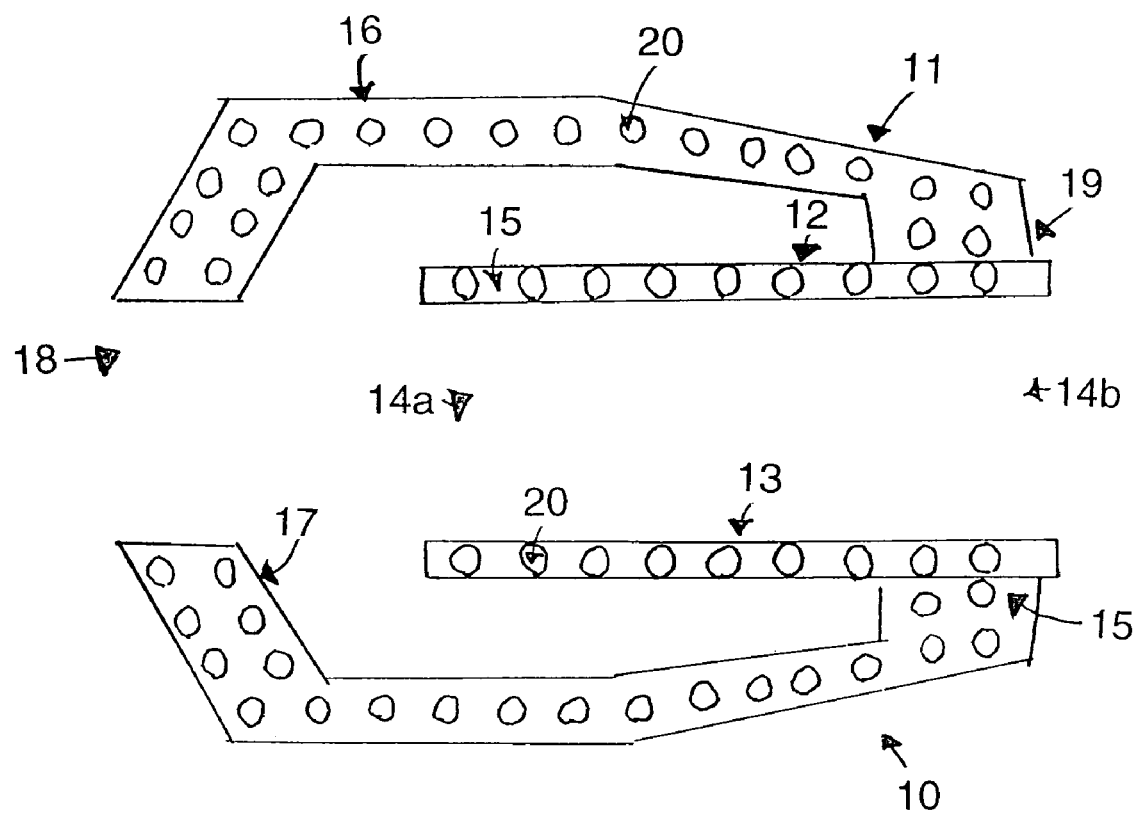
FIG. 6A depicts the device of FIG. 2 having a second part containing embedded conductors.
Figure 6B:
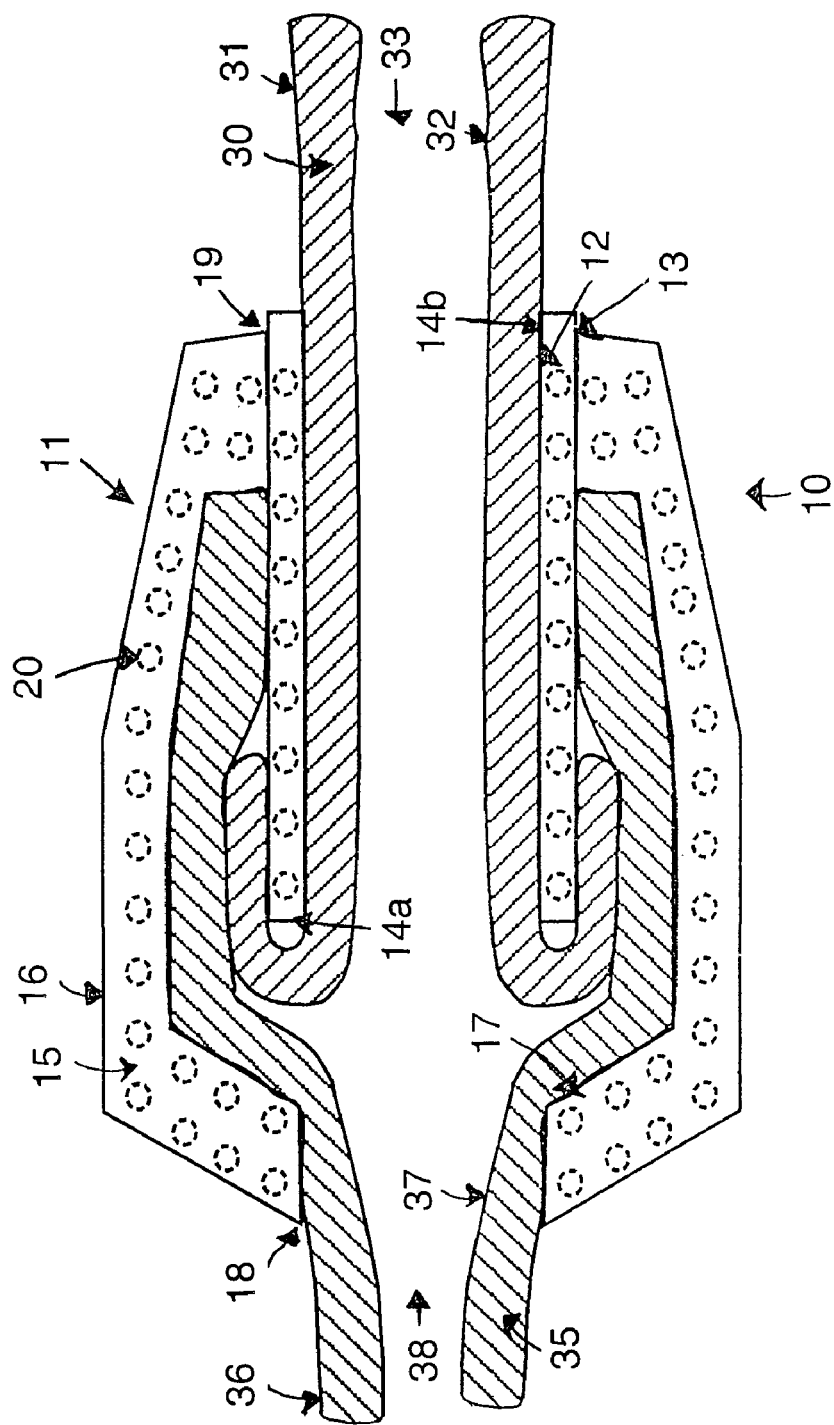
FIG. 6B depicts the device emplaced around a site of anastomosis.

The appendage to the tubular material is attached to the tubular material at one end, extends out and over the tubular material to a distance beyond the first open end of the tubular material and is open at this same end as the tubular fusion material. The diameter across the inner surface at the open end of the appendage is equal to the inner diameter of the tube (FIG. 6A). Thus, when the tubular material is emplaced so that the healthy vessel and the graft tissue or material are averted around the first open end, the appendage fits over the outer surface of the vessel to be anastomosed and is in contact with the vessel along that outer surface (FIG. 6B).

This allows the outer surface of the vessel to be heated when a brief electrical pulse is applied to the conductive element. The pulse may be in the form of a unspooled or bipolar pulse of direct current, which depending on the material that makes up the conductive element, may be as small as a few volts and milliamps. The temporal extent of the pulse can be as short as about a few microseconds and multiple pulses may be required to obtain the desired effect. Longer pulses may also be used, however, an overproduction of heat might induce undesirable damage to the proximal tissue. Generally, the pulse should be brief enough and of enough magnitude to induce heating of the conductive element so that the threshold for a particular molecular change of the biocompatible material and of the outer surface of the vessel and bypass graft is exceeded. A temperature contemplated for such a molecular change is about 85° C.

Applicator

Applicator geometry greatly affects the distribution of the resultant electromagnetic field. Several different designs for the applicator are possible. The most efficacious design depends on the procedure for which the applicator is intended.

For induction heating, a coil of wire may be connected to an activator in order to produce a strong and uniform magnetic field along the long-axis of the coil (FIG. 7) and is most suitable for inductively heating materials positioned within the turns of the coil. Alternatively, the magnetic field can be externalized from the interior of the coil with the use of a core material, such as used in transformers. The core material may be a magnetic material and, optionally, a powdered magnetic material so that heat production in the core is minimized.

Figure 8A:
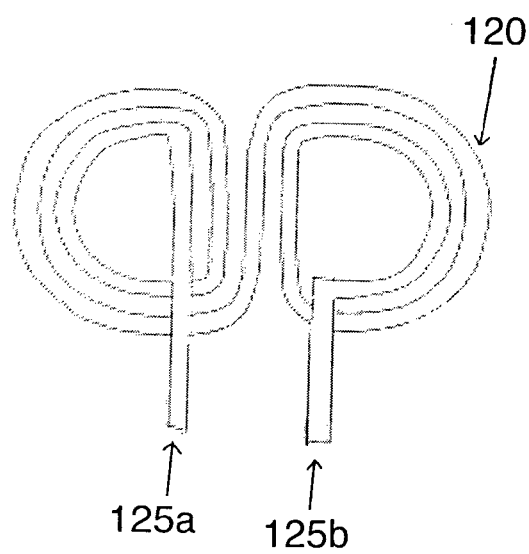
FIGS. 8A-8D depict three differently shaped flat pancake coils (FIGS. 8A-8C) and a containment means for cooling the coil in FIG. 8B (FIG. 8D).
Figure 8B:
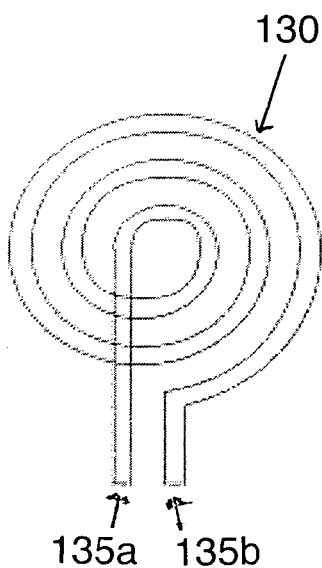
Figure 8C:
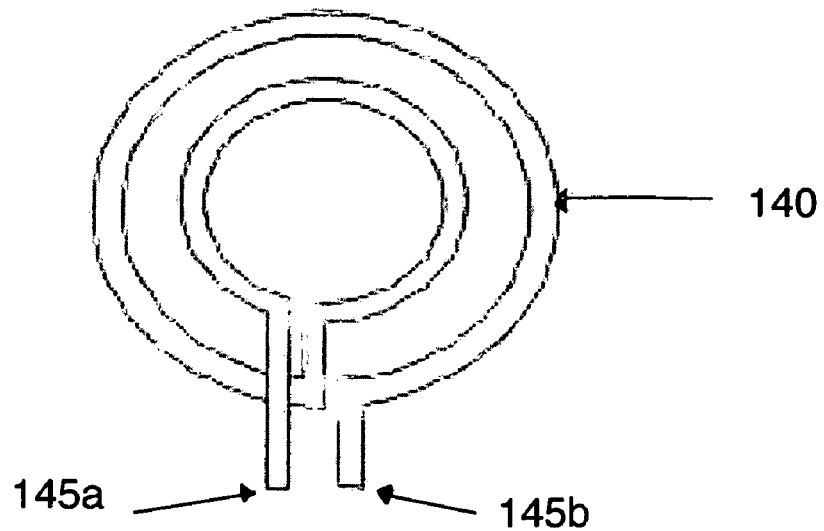

Other applicator designs allow for, a relatively strong magnetic field to be produced exterior to the wire or tubing. For example, the designs shown in FIGS. 8A-8C are three examples of applicators whereupon the field is produced above or below the plane of the conductor. In FIG. 8A, the strongest field is produced below each separate coil while in FIGS. 8B and 8C, the strongest field is produced in a single position below the coil.

Figure 9A:
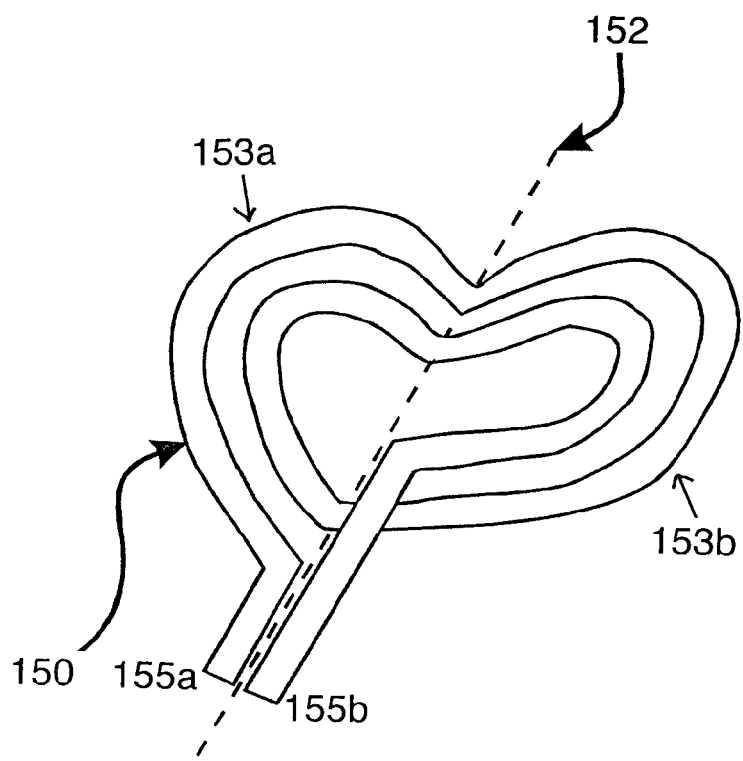
FIGS. 9A-9B depict a pancake coil with a non-planar geometry (FIG. 9A) and a conical spiral coil geometry (FIG. 9B).
Figure 9B:
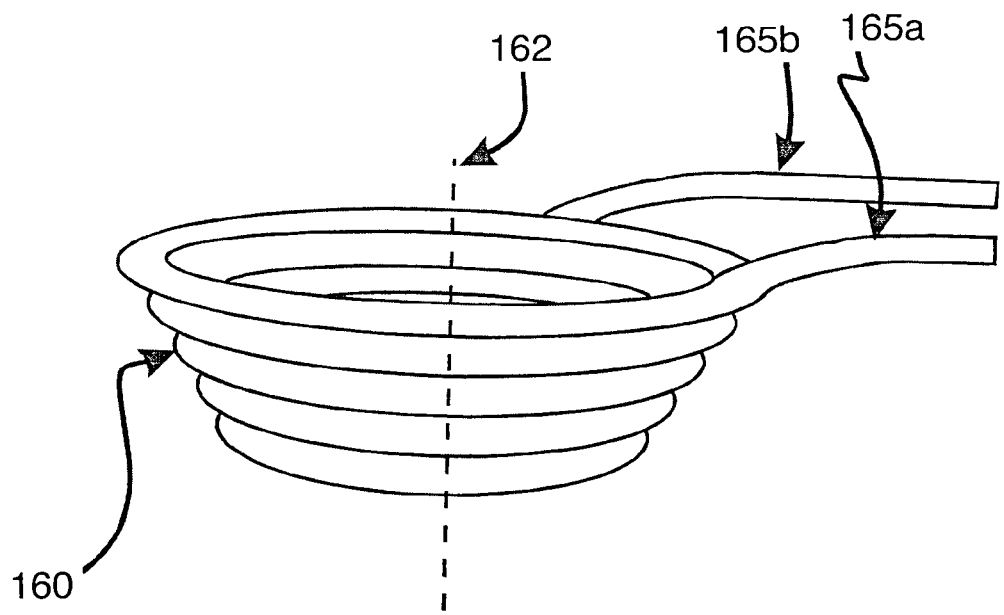
Figure 9C:
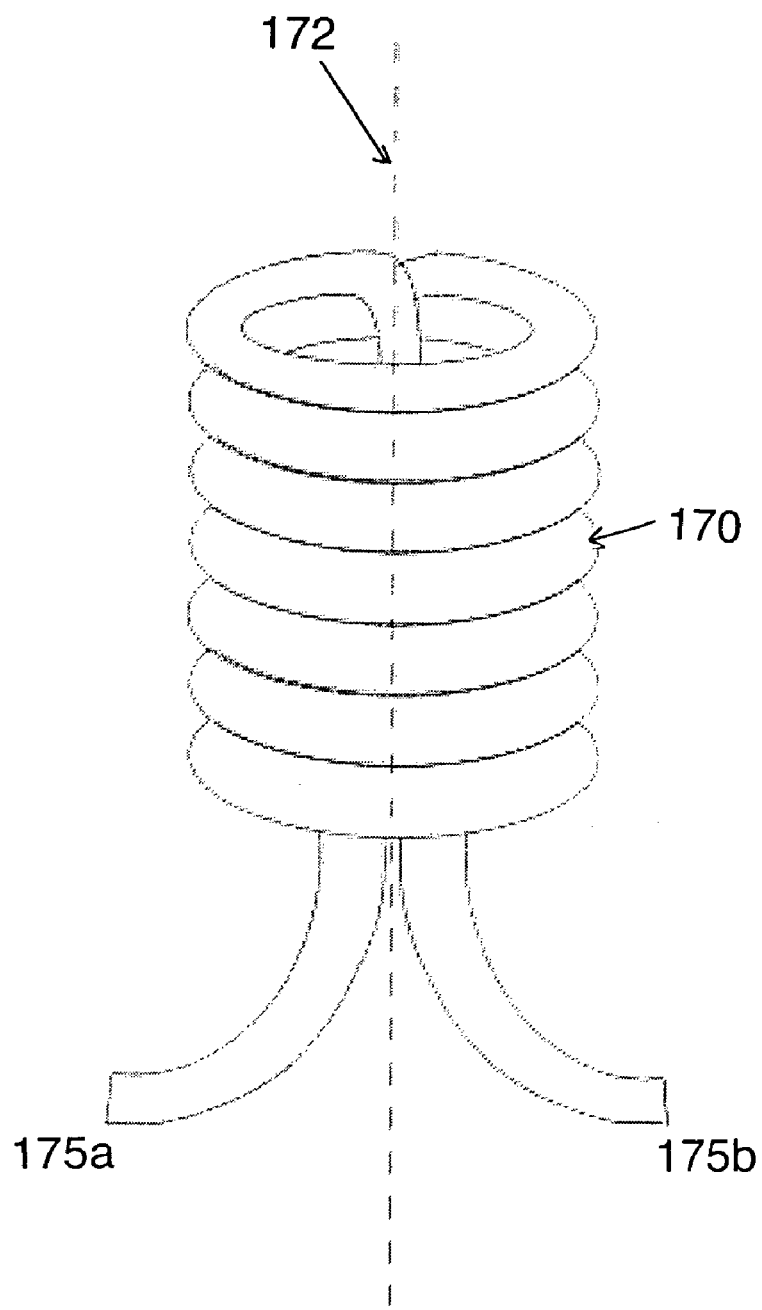
FIG. 9C depicts an applicator coil suitable for use within tubular structures such as blood vessels.

The applicator also may be bent into a particular shape, as demonstrated in FIGS. 9A-9B, whereupon the distance between the material to be heated and the conductor that makes up the applicator is minimized. This provides for an efficient use of energy. Additionally, the applicator may be shaped to be symmetric around an axis and is designed for use in a hollow anatomical structure, such as a blood vessel (FIG. 9C).

Optionally, a ferromagnetic material, e.g. pole-piece, may be partially positioned in the magnetic field produced by the applicator thereby allowing the field to be transferred to the end of the pole-piece thus producing concentration of the field lines and providing greater accessibility to the field. At high frequencies, it may be beneficial for this pole piece to be made substantially from powdered ferromagnetic materials in order to minimize undesirable heating in the pole piece itself.

If required, the coil can be cooled by encapsulating it in a glass envelope through which a cooling fluid, such as low viscosity mineral oil, can be circulated. Cooling is enhanced by using a hollow tubing, such as copper, through which a cooling fluid such as water can be circulated. The advantage therein is that the dielectric property of the cooling fluid is irrelevant because it is contained within the conducting coils and not on the outside where it would be inductively coupled to the produced magnetic field. Optionally, the tubing material may be coated in a biocompatible non-stick material, such as teflon, so that heated tissue will not adhere to the applicator.

Figure 10A:
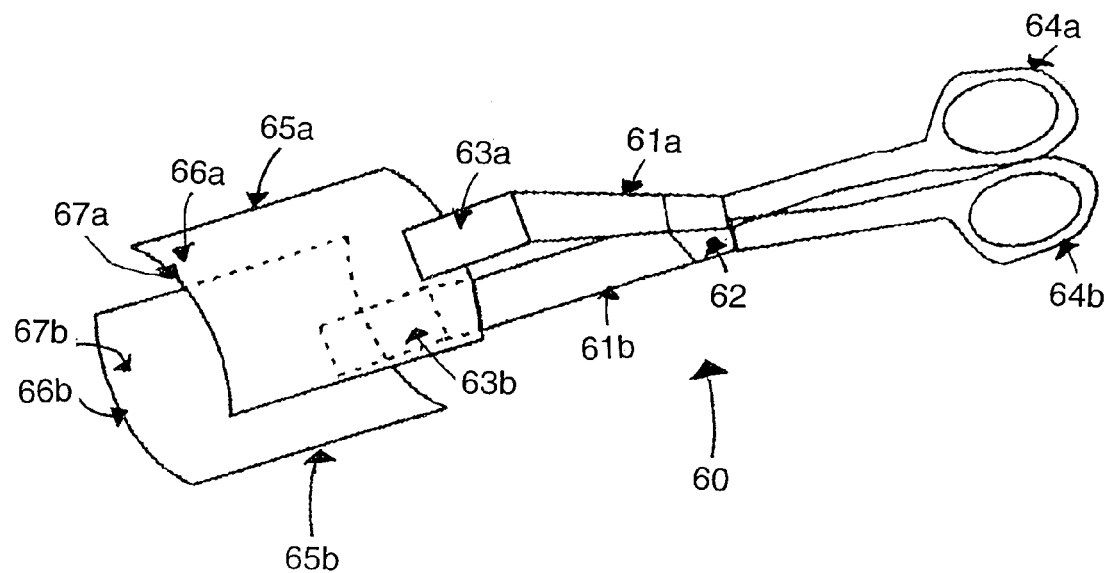
FIG. 10A depicts a device that can be used to provide an internal alternating magnetic field that is used to inductively heat a biocompatible fusion material.
Figure 10B:
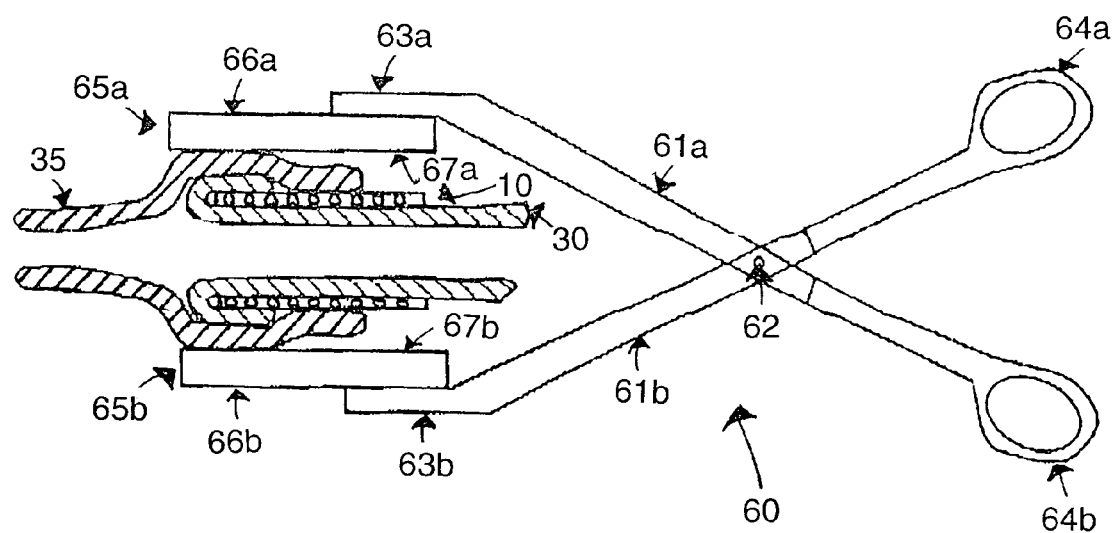
FIG. 10B depicts the positioning of the device around tissues to be anastomosed.
Figure 11:
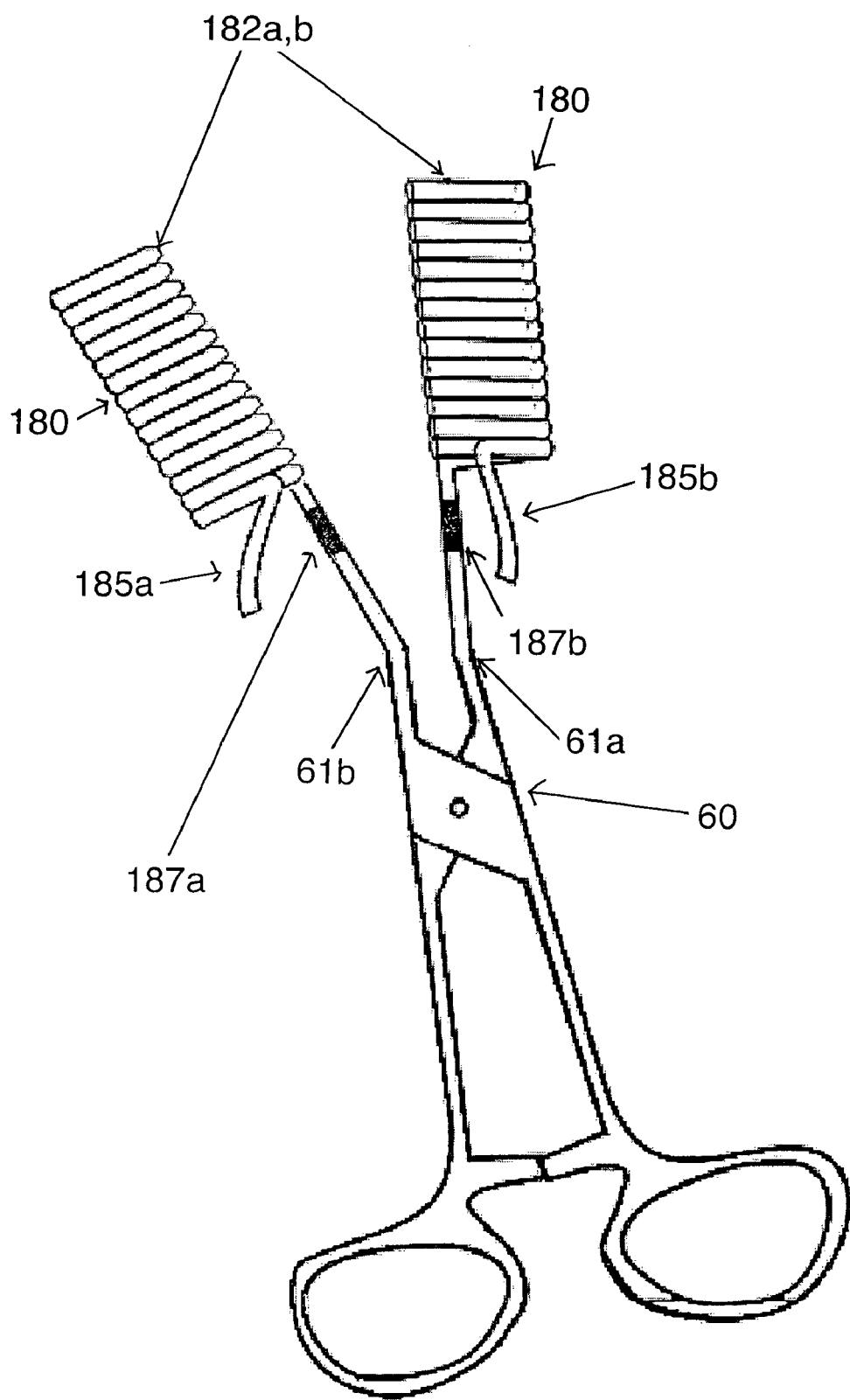
FIG. 11 depicts a coil applicator that can be split thus allowing positioning of tissue in the interior of the coil.

An oscillating magnetic field may be applied using an instrument having two separate coils attached independently to the ends of a clamp-like extension (FIG. 10A). The coils can be coated in a smooth non-adhering material which comprises, for example, teflon, titanium or gold. Using the scissors-like action of the clamp, the instrument is positioned around and proximal to the biocompatible fusion material such as around the tubular configuration used for vascular anastomoses (FIG. 10B). The coils can be attached to a radiofrequency power supply or activator that produces the oscillating magnetic field within the coils. Alternatively, a single coil may be made in such a way that it can be opened up thus allowing a tissue, such as a blood vessel, to be positioned within the coil which then closes and completes the circuit (FIG. 11).

Activator

The power-supply can produce radiofrequency energy with a power in the range 10-10,000 W and may typically operate at frequencies of 100 kHz to 5 GHz. The best operating frequency depends, inter alia, on the nature of the fusion composition to be heated, the geometry of the tissue to be fused or the cavity to be filled and regulatory criteria. The output impedance of the power-supply is preferably matched to the input impedance of the applicator.

The power-supply has several safety features incorporated. For example, the output is optionally low voltage, i.e., <50V, and the device is shielded for emitted or received electromagnetic-interference. Thermal switches are incorporated within the device to shut it down if overheating occurs. Fast breakers quickly cut off the output if a power-output transient occurs. Multiple interlocks are incorporated into the device which prevent running the device with the cover removed. A foot pedal is optionally incorporated in order to minimize the possibility of unintentional activation of the device.

The tissue fusion devices of the present invention are useful for treating tissue in an individual or animal to effect a fusion or bond between two or more elements of tissue. The TFD utilizes at least one biocompatible material comprising a substance which functions as a bonding agent between the tissue and the material(s) interspersed with a conductive element, the activator and applicators described herein and a means to control the amplitude and persistence time of the field. The method may be used to effect a sealing of a sinus in tissue whereby the biocompatible material functions as a sealing agent.

The tissue fusion devices may be used to effect a fusion between a tissue and at least one material. The TFD is placed on the tissue of the individual whereupon high frequency electrical energy is delivered to the conductive element within the device or inductively heating the conducting element within the device. The TFD is monitored to control the extent of the weld between the tissue and the material(s).

Control may be exerted by direct feedback monitoring of heat generation or by prediction and measurement of the magnetization of the composition over time with regard to its volume and mass. This feedback may arise from measurements of impedance changes in the applicator, as the tissue becomes part of the circuit during treatment, or devices such as thermocouples or infrared thermometers can be employed. A second order of control may be exerted through the use of ferromagnetic metals and alloys as susceptors that remain magnetized until reaching a critical temperature, i.e., the Curie temperature, whereupon they cease to be magnetic.

As described below, the invention provides a number of therapeutic advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

FIG. 1 depicts a device 10 having an essentially tubular structure which is formed from preferably a biocompatible material 15. The tubular device 10 has an outer surface 12 and an inner surface 13 and has a first open end 14a and a second open end 14b.

In FIG. 2 and with continued reference to FIG. 1, a conducting element 20 is incorporated within the material 15 comprising the tubular device 10. The conducting element 20 is helically shaped and is embedded between the outer 12 and inner 13 surfaces of the tubular device 10 and coils from a first end 21a at the first open end 14a of the device 10 to a second end 21b at the second open end 14b of the device 10.

With continued reference to FIG. 2, FIGS. 3A and 3B depict a cross-section of the tubular device 10 with alternate placements of the conductive element(s) 20 within the biocompatible material 15. The conductive elements 20 can be placed symmetrically throughout the tubular device 10 for uniform heating of the biocompatible material 15 of the device 10 as demonstrated in FIG. 3A. Alternatively, the conductive elements 20 can be embedded asymmetrically within the biocompatible material 15 to provide more heat where it is needed, such as at the site to be anastomosed as shown in FIG. 3B.

With continued reference to FIGS. 3A and 3B, FIG. 4 depicts a cross-section of the tubular device 10 having an electromagnetic energy-absorbing material 25, more particulate in structure than the conducting elements 20, that is distributed within the biocompatible material 15. Distribution of the energy-absorbing material 25 is similar to that of the asymmetrical placement of the conducting element 20.

Figure 5:
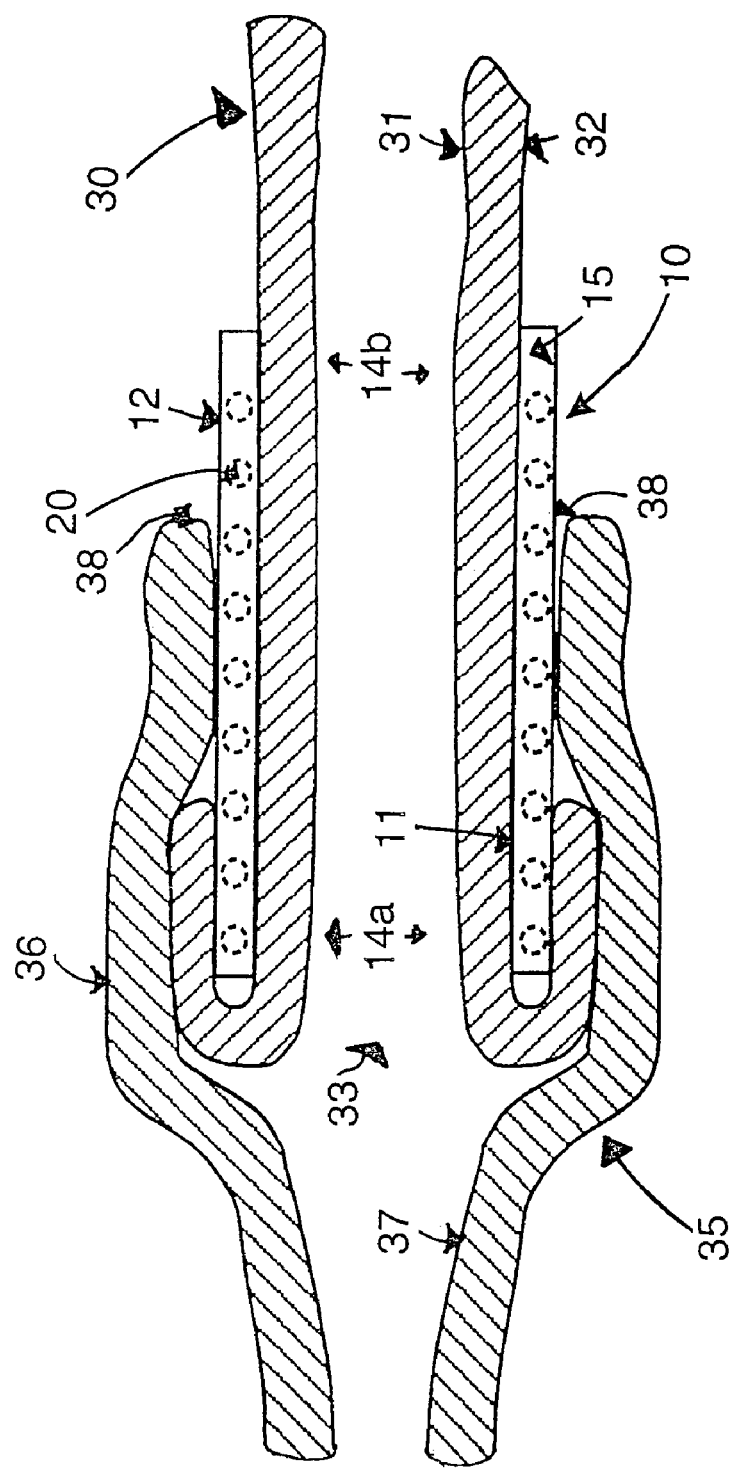
FIG. 5 depicts cross-sectional view A-A of the device of FIG. 2 positioned between two separate ends of a blood vessel which are to be anastomosed.

With further reference to FIG. 2, FIG. 5 depicts a cross-section of the device 10 as it is emplaced. The tubular device 10 containing the conducting element 20 or energy-absorbing material 25 is fitted over the graft tissue 30 such that the outer surface 36 of the graft tissue 30 is in contact with the inner surface 13 of the tubular device 10. The graft 30 is positioned so that an open end 33 of the graft 30 is averted around the first open end 14a of the device 10 such that the outer surface 31 of the averted end 33 of the graft 30 is in contact with the outer surface 12 of the tubular device 10. The device 10 containing the averted graft tissue 30 is placed within the opening 38 of the healthy vessel 35 to be anastomosed such that the inner surface 37 of the vessel 35 is in contact with both the averted end 33 of the graft tissue 30 and the outer surface 11 of the tubular device 10. Application of an electric current to the conducting elements 20 or the energy-absorbing material 25 would heat the biocompatible material 15 and effect a molecular change within the material 15 and within the graft tissue 30 and the healthy vessel 35 such that cooling of the biocompatible material 15 results in an anastomosis of the tissues 30, 35.

Continuing to refer to FIGS. 2 and 5, FIG. 6 depicts a cross-sectional view of an alternate structure and emplacement for the tubular device 10. The device 10 has an appendage part 11 surrounding the tubular device 10. The appended part 11 has an outer surface 16 and an inner surface 17 and has a first open end 18 and a second end 19 which is attached to the outer surface 12 of the tubular device 10 at the second open end 14b of the tubular device 10. The appendage 11 extends out and over the tubular device 10 from the attached second end 19 toward the first open end 14a of the tubular device 10. The inner diameter of the first open end 18 of the appendage 11 and the inner diameter of the first open end 14a of the tubular device 10 are about equal. The first open end 18 of the appendage 11 is at a distance from the first open end 14a of the tubular device 10 sufficient to accommodate the graft tissue 30 and the healthy vessel 35 averted around the first open ends 14a,18 of the tubular device 10 and the appendage 11. The appendage 11 may comprise the conductive element 20 or the energy-absorbing material 25 distributed within the material 15 of the tubular device 10 as depicted in FIGS. 3A, 3B or 4.

As shown in the cross-sectional view depicted in FIG. 6B, when the tubular device 10 is emplaced as demonstrated in FIG. 5, the open end 38 of the healthy vessel 35 is averted around the open first end 18 of the appendage 11 such that the inner surface 17 of the appendage 11 is in contact with the outer surface 36 of the healthy vessel 35. As in FIG. 5, application of an electric current to the conducting elements 20 or the energy-absorbing material 25 would heat the biocompatible material 15 in both the tubular device 10 and the appendage 11 and effect a molecular change within the material 15 and within the graft tissue 30 and the healthy vessel 35 such that cooling of the biocompatible material 15 results in an anastomosis of the tissues 30, 35.

Figure 7:
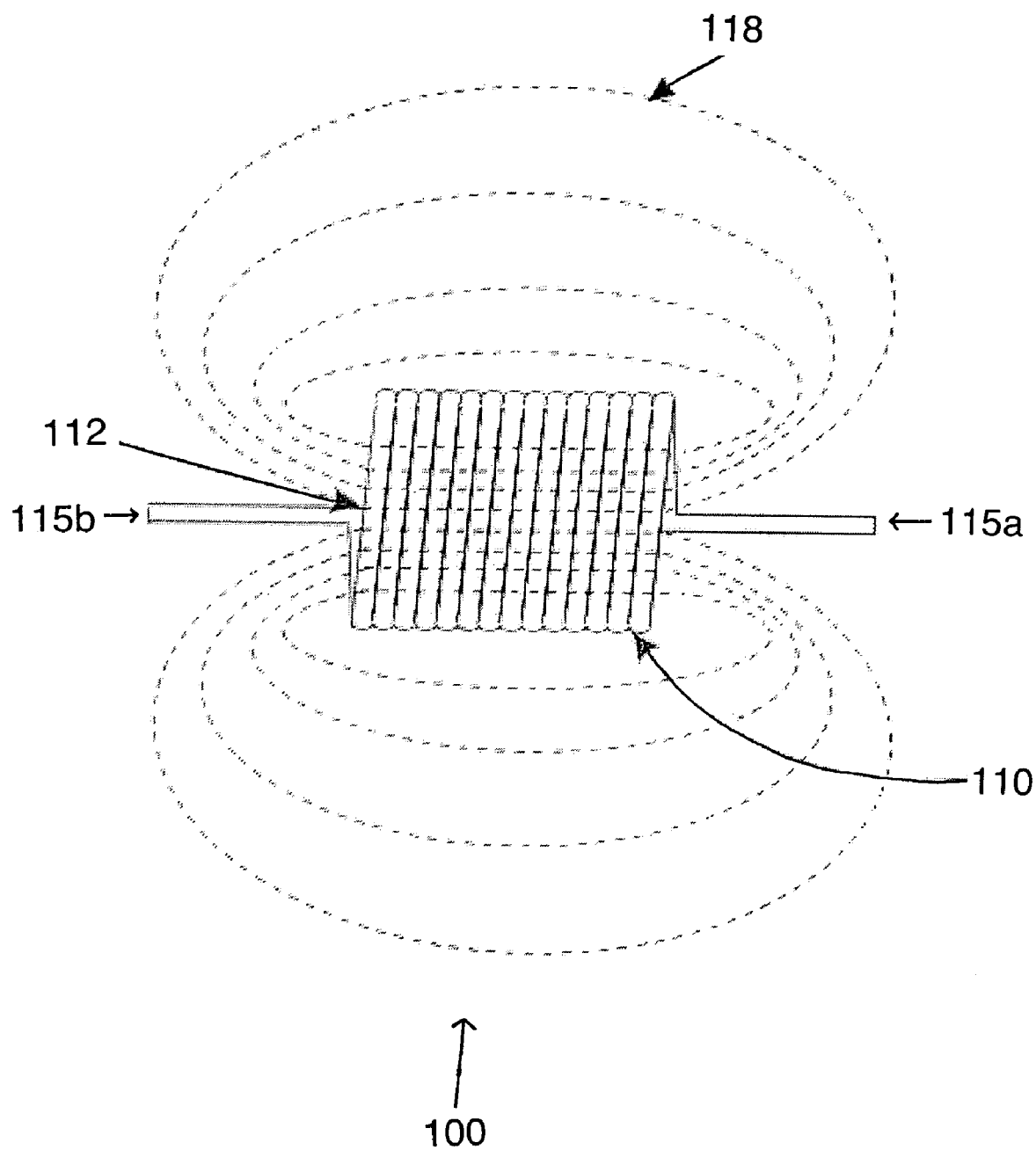
FIG. 7 depicts a solenoid-type coil applicator carrying an electrical current and the resultant magnetic field lines.

FIG. 7 depicts an applicator 100 having an essentially solenoid coil structure 110 which is formed with an interior cylindrical zone 112. The solenoid coil 110 has electrical connectors 115a,b. The magnetic field lines 118 produced when an electrical current is passed through the electrical connectors 115a,b is shown. While the greatest magnetic intensity H (A/m) occurs within the applicator, a weaker magnetic field occurs at the ends and outside of the solenoid 110.

Figure 8D:
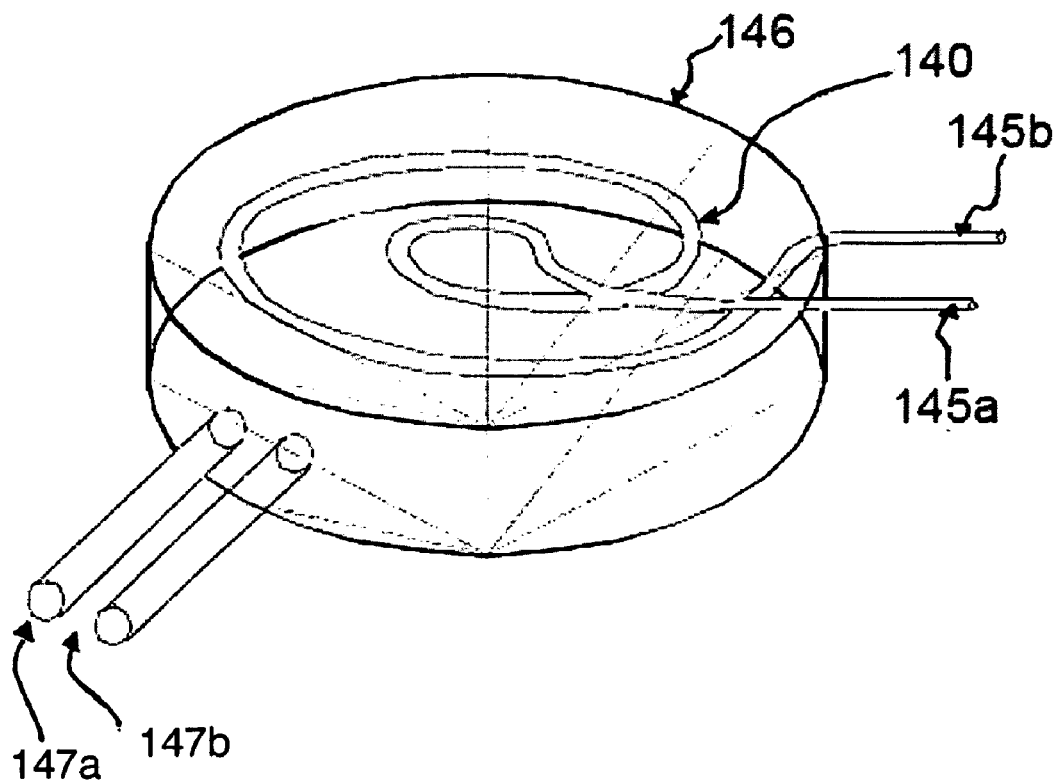

FIGS. 8A-8C depict substantially flat applicator coils for activating in other anatomical geometries. FIG. 8A shows a "butterfly coil" 120 with electrical connectors 125a,b. FIGS. 8B-8C show a spiral coils 130 with electrical connectors 135a,b and spiral coil 140 with electrical connectors 145a,b, respectively. Each coil 120, 130, 140 produces a magnetic field with a particular geometric shape. Coil 120 produces a two-lobed shaped field above and below the flat plane of the coil (not shown). With the addition of a material, such as mumetal, it is possible to shield the superior surface of the coil if no magnetic field is desired above the coil. FIG. 8D depicts the spiral coil 140 positioned within a cooling fluid envelope 146, optionally made of glass, through which cooling fluid can be circulated by introducing and extracting cooling fluid through the apertures 147a,b. Optionally, the cooling fluid can be circulated through the spiral coil 140 itself by being introduced and extracted through the electrical connectors 145b and 145a.

In FIG. 9A and with continued reference to FIG. 10B, a non-planar coil applicator 150 is illustrated. The coil 150 with electrical connectors 155a,b is similar to coil 130 in FIG. 10B, but each half 153a,153b of coil 150 is bent towards the centerline 152, thus increasing the magnetic field intensity H at a position within a volume contained within the bent coil 150. FIG. 9B depicts a coil 160 with electrical connectors 165a,b which is in the form of a conical spiral with axis of symmetry 162. FIG. 9C shows a fusion applicator coil 170 with electrical connectors 175a,b which is symmetrical around axis 172 and which is designed for use in a hollow anatomical structure, such as a blood vessel (not shown).

FIG. 10A depicts a clamp-like instrument 60 with which to apply an external oscillating magnetic field. The instrument 60 comprises a scissors-like extension having two arms 61a,b pivotally connected at the center 62. The arms 61a,b have a first end 63a,b attached to a coil 65a,b and have a second end 64a,b comprising a gripping means. The coils 65a,b form an essentially planar structure each having an outer surface 66a,b and an inner surface 67a,b and are each attached to a first end 63a,b of the arms 61a,b so that the inner surfaces 67a,b of the coils 65a,b are juxtaposed essentially horizontally and in parallel to each other. The pivotal action of the arms 61a,b increases or decreases the distance between the inner surfaces 67a,b of the inductive coils 65a,b such that the coils 65a,b may be positioned around a site of anastomosis. The inductive coils 65a,b are attached to a radiofrequency source (not shown).

FIG. 10B depicts the positioning of the instrument 60 around a site to be anastomosed where the tubular device 10 is emplaced as shown in FIG. 5. The inductive coils 65a,b are designed such that when positioned around an anastomosis site the inner surfaces 67a,b of the coils 65a,b are in contact with the outer surface 36 of the healthy vessel 35 at the point where the healthy vessel 35 is averted around the graft tissue 30 and the tubular device 10. Application of radiofrequency to the coils 65a,b induces a magnetic field which heats the conducting elements 20 or the energy-absorbing material 25 in the biocompatible material 15 of the tubular device 10 and, as in FIG. 5, effect a molecular change within the material 15 and within the graft tissue 30 and the healthy vessel 35 such that cooling of the biocompatible material 15 results in an anastomosis of the tissues 30, 35.

FIG. 11, with continued reference to FIGS. 7 and 10A, depicts a solenoid-type applicator coil 180 constructed such that it can be opened, thus allowing the positioning of an anatomical structure (not shown) within the interior cylindrical zone. The coil halves 182a,b are attached to a clamping device 60 as depicted in FIG. 10A. When the coil-halves 182a,b are closed, they establish electrical contact and so the resulting intensity H is consistent with the field 118 shown in FIG. 7. The clamping device 60 is electrically isolated from the coil 180 by insulators 187a,b, placed at the arms 61a,b of the clamping device 60. Power is conducted to the coil halves 182a,b with electrical connectors 185a,b.

Figure 12:
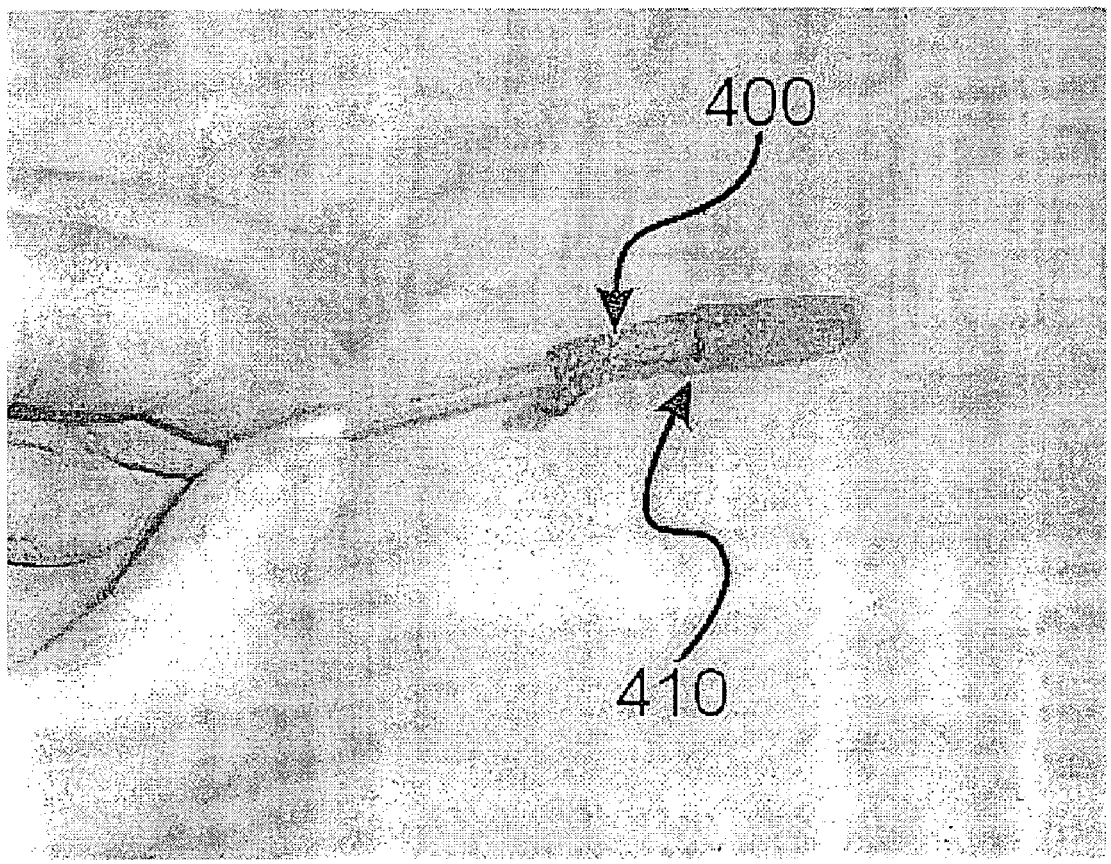
FIG. 12 depicts an ovine blood vessel anastomosed with an activator, applicator, and fusion composition.

FIG. 12 depicts the visible fusion 410 of a vascular vessel 400.

Figure 13:
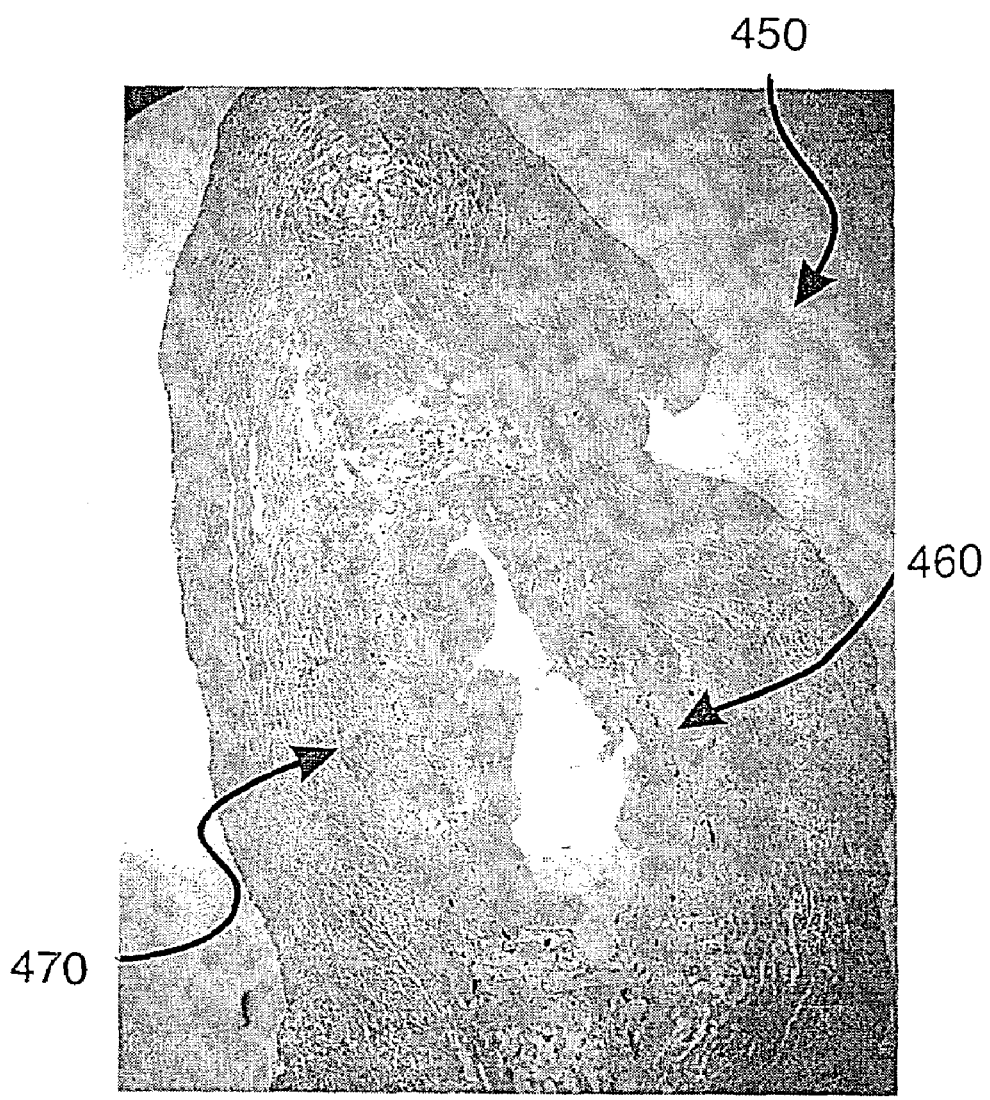
FIG. 13 depicts a histologic section through a blood vessel anastomosed via the tissue fusion device.

FIG. 13, with reference to FIG. 12, shows a histological section of the vascular vessel 400 with metallic particles 430 and 440 at the interface 410 between the two overlapping sections.

The following examples are given for the purpose of illustrating various embodiments of the invention and are not meant to limit the present invention in any fashion.

EXAMPLE 1

Heating of Test Metal

The tissue fusion activator device constructed operates at a frequency of about 650 kHz and has an output of approximately 210 W. At or near this frequency, the skin depth in tissue for canine skeletal muscle at 1 MHz (10) is about 205 cm, while for nickel it is 160 μm. Thus, no significant heating of tissue occurs as a direct result of the field. Heating only occurs in close proximity to the fusion composition. Two solenoid-type applicator designs were used, and were made up of 200 turns of solid copper wire, 32 and 22 G, thus resulting in a coil approximately 2.86 cm in diameter and 0.95 cm in width. The bore of the coil was about 0.5 cm. The coils were encapsulated in a Pyrex sleeve, through which low-viscosity mineral oil (Sigma-Aldrich Inc., St. Louis, Mo.) was circulated as a coolant. In each of these coils, the magnetic intensity at the center of the coil is calculated to be greater than 10,000 A/m, while at approximately 0.5 cm from a single coil face the intensity is calculated to be maximally 160 A/m.

The blade of a small screwdriver (Craftsman Model 41541, 3.15 mm diameter) was positioned within the bore of the coils. After 1-5 seconds, the screwdriver was extracted and the blade was brought into brief contact with the skin of the hand. It was immediately apparent that significant heating had taken place in the blade of the screwdriver.

EXAMPLE 2

Heating and Coagulating of Test Fusion Formulation

Fusion formulations were made of 50-75% (w/v) albumin (Bovine serum, or ovalbumin; Sigma-Aldrich, St. Louis, Mo.) in saline with a metal additive of 5% or 10% (w/v) nickel flake (average particle size=50 micron, Alfa Aesar, Ward Hill, Mass.) or 10% iron filings (particle size <30 microns; Edmund Scientific, Tonawanda, N.Y.)). Aliquots of approximately 1 ml of the fusion composition was positioned in thin-walled glass tubes with a diameter of about 4 mm. The tube was then positioned in the bore of the applicator. The device was energized for a period of 20-30 seconds. Evidence of denaturation and coagulation was ascertained visually as the material changed color. This was confirmed by probing the composition with a needle, which demonstrated evidence of increased viscosity or stiffness. The composition coagulated with all combinations of applicator and composition. Compositions with more metal or iron versus nickel heated at different rates.

EXAMPLE 3

Fusion of Vascular Tissue

A series of experiments were performed using donated carotid, femoral and brachial artery samples harvested from sheep. The samples were rinsed in physiologic saline, placed in wet gauze, and frozen at −20° C. before use. After thawing, each sample was bisected lengthwise with a scalpel. The fusion formulation of 5% Ni and 50% albumin was placed around the periphery of one end of a bisected sample, i.e. on the adventitia, and the end of the other bisected sample was manually dilated and pulled over the fusion formulation so that there was an overlap of a few millimeters. A glass rod was positioned within the intima of the two vessels as a support to hold the tissue in place. The sample was then positioned between the faces of two opposing solenoid-type applicators, and the sample exposed to approximately 210 W of power for about 30 seconds.

As seen in FIG. 12, fusion of the vessel 400 was visually apparent 410, and the fused tissue could not be teased apart with forceps without damage to the tissue. There was no visual evidence of burning. Tests were repeated five times with equivalent results. The vessels were placed in 10% formalin, sectioned transversely, or perpendicular to the long-axis of the vessel, across the fused area and submitted for histological preparation and staining with hematoxylin-eosin. A sample histologic section is presented in FIG. 13 which shows the vessel 400 and the presence of metallic particles 430 and 440 at the interface between the two overlapping sections.

The following references are cited herein:
1. Bass, L S and Treat, M R. Laser Surg. Med. 17, 315-349 (1995).
2. Freid, N M and Walsh, J T. Lasers Surg. Med. 27, 55-65 (2000).
3. Davies E J. Conduction and Induction Heating. Inst. Elect. Engs. and P. Peregrinus:London (1990).
4. Orfeuil M. Electric Process Heating: Technologies/Equipment/Applications. Battelle Press: Columbus Ohio (1987).
5. Zinn S. and Semiatin S L. Elements of Induction Heating-Design, Control and Applications, Electric Power Research Institute: Palo Alto, Calif. (1988).
6. Stauffer P R, Cetas R C and Jones R C. IEEE Trans. Biomed. Eng. BME-31, 235-251 (1984).
7. Jordan A. et al, Int. J. Hyperthermia. 13(6):587-605 (1997).
8. Hamad-Schifferli K, Schwartz J J, Santos A T, Zhang S and Jacobson J M., Nature 415, 152-155 (2002).
9. Damodaran S. Int. J. Biologic. Macromolec. 11, pp.2-8 (1989).
10. Francis Duck. Physical Properties of Tissue-A Comprehensive Reference Book. Academic Press: NY (1990).

Any patents or publications mentioned in this specification are indicative of the levels of those skilled in the art to which the invention pertains. These patents and publications are herein incorporated by reference to the same extent as if each individual publication was incorporated specifically and individually by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A device for creating an anastomosis of tissue(s) comprising:
    a fusable biocompatible material;
    a conductive material combined with the biocompatible material,
    at least one induction coil disposed in relation to the biocompatible material such that a radiofrequency-induced oscillating magnetic field generates heat around the biocompatible material to fuse or bond at least two materials and create anastomosis of tissue(s); and
    a glass envelope containing a cooling fluid and said induction coil(s).

2. The device of claim 1, wherein said biocompatible material complements tissue geometry to bond or fuse at least two materials wherein at least one material is a tissue.

3. The device of claim 1, wherein said biocompatible material is a liquid, a solid or a semi-solid.

4. The device of claim 1, wherein said biocompatible material comprises a protein, a biocompatible polymer, polymeric matrix substance, or a combination thereof.

5. The device of claim 4, wherein said protein is elastin, albumin, fibrin, collagen, or glycoprotein.

6. The device of claim 4, wherein said polymeric substance is hydrogel, agar or sol-gel.

7. The device of claim 4, wherein said biocompatible material further comprises a pharmaceutical.

8. The device of claim 7, wherein said pharmaceutical is an anti-coagulant, an antithrombotic, an antibiotic, a hormone, a steroidal antiinflammatory agent, a non-steroidal antiinflammatory agent, an anti-viral agent or an anti-fungal agent, or a combination thereof.

9. The device of claim 1, wherein said cooling fluid is low viscosity mineral oil or water.

10. The device of claim 1, wherein said induction coils further comprise a coating of a smooth non-adhering material.

11. The device of claim 1, wherein said non-adhering material comprises polytetrafluoroethylene, titanium or gold.

12. The device of claim 1, wherein the conductive material has a thermal history such that application of the oscillating magnetic field to said conductive material generates an estimable amount of heat.

13. The device of claim 1, wherein said conductive material is a metal wire, a metal particle, a ferromagnetic material, a paramagnetic material, a conducting polymer, an ionic molecule, a polar molecule or a conducting microsphere.

14. The device of claim 1, wherein said conductive material is an energy-absorbing material, said energy-absorbing material comprising conducting polystyrene microbeads, a colloidal metal, a conducting polymer, a strongly ionic molecule or a strongly polar molecule.

15. A method for performing an anastomosis between at least two tissues comprising the steps of:
    positioning the device of claim 1 around said tissues, said tissues simultaneously in contact with the biocompatible material of said device and with each other;
    applying a radiofrequency-induced oscillating magnetic field to said biocompatible material; thereby generating heat within one or both of said biocompatible material or conductive material and said tissues, said heating adhering said biocompatible materiel to said tissues, or adhering said tissues to each other, thereby anastomosing said tissues.

16. The method of claim 15, wherein adherence of said biocompatible material to said tissues or adherence of said tissues results from molecular changes in said biocompatible material and in said tissues.

17. A device for fusing at least two materials, whereby at least one material is tissue, comprising:
    a fusable biocompatible material;

at least one induction coil disposed in relation to the biocompatible material such that a radiofrequency-induced oscillating magnetic field generates around the biocompatible material;

a glass envelope containing cooling fluid and said induction coil(s); and means for controlling output of the heat generated within said biocompatible material and combined therewithin.

18. The device of claim 17, wherein said biocompatible material complements tissue geometry.

19. The device of claim 17, wherein said biocompatible material is a liquid, a solid or a semi-solid.

20. The device of claim 17, wherein said biocompatible material comprises a protein, a biocompatible polymer, polymeric matrix substance, or a combination thereof.

21. The device of claim 20, wherein said protein is elastin, albumin, fibrin, collagen, or glycoprotein.

22. The device of claim 20, wherein said polymeric substance is hydrogel, agar or sol-gel.

23. The device of claim 20, wherein said biocompatible material further comprises a pharmaceutical.

24. The device of claim 23, wherein said pharmaceutical is an anti-coagulant, an antithrombotic, an antibiotic, a hormone, a steroidal antiinflammatgry agent, a non-steroidal antiinflammatory agent, an anti-viral agent or an antifungal agent, or a combination thereof.

25. The device of claim 17, wherein said cooling fluid is low viscosity mineral oil or water.

26. The device of claim 17, said induction coils further comprising a coating of a smooth non-adhering material.

27. The device of claim 26, wherein said non-adhering material comprises teflon, titanium or gold.

28. The device of claim 17, wherein the means for controlling output of heat conducted to said tissues is a conductive material in contact with said biocompatible material, said conductive material having a thermal history such that application of the oscillating magnetic field to said conductive material generates an estimable amount of heat.

29. The device of claim 28, wherein said conductive material is a metal wire, a metal particle, a ferromagnetic material, a paramagnetic material, a conducting polymer, an ionic molecule, a polar molecule or a conducting microsphere.

30. The device of claim 28, wherein said conductive material is an energy-absorbing material, said energy-absorbing material comprising conducting polystyrene microbeads, a colloidal metal, a conducting polymer, a strongly ionic molecule or a strongly polar molecule.

31. A method for fusing two materials, whereby at least one is tissue, comprising the steps of:

positioning the device of claim 17 around said materials, said materials simultaneously in contact with the biocompatible material of said device and with each other;

applying a radiofrequency-induced oscillating magnetic field to said biocompatible material;

generating heat within said biocompatible material; and controlling output of heat to said materials to be fused via the heat controlling means of said device, said output of heat fusing said materials together.

32. The method of claim 31, wherein bonding of said biocompatible material to said materials or fusing said materials together results from molecular changes in said biocompatible material and in said materials.

* * * * *